United States Patent [19]

Calleja

[11] Patent Number: 5,406,964
[45] Date of Patent: Apr. 18, 1995

[54] METHOD FOR PROTECTING AN INFANT'S NAVEL

[76] Inventor: Antonio M. Calleja, Calle de la Merce, no 24, 08393 Caldes D'Estrac, Bareelona, Spain

[21] Appl. No.: 183,779

[22] Filed: Jan. 21, 1994

Related U.S. Application Data

[63] Continuation of Ser. No. 873,657, Apr. 23, 1992, abandoned, which is a continuation of Ser. No. 573,729, Aug. 28, 1990, abandoned.

[30] Foreign Application Priority Data

Aug. 29, 1989 [ES] Spain .............................. 8902666 U

[51] Int. Cl.$^6$ .............................................. A61F 13/00
[52] U.S. Cl. ................................... 128/888; 128/846; 602/53; 2/311
[58] Field of Search .............. 128/846, 869, 888, 889; 602/1, 19, 41, 53, 67; 450/94, 98, 155; 2/44, 311, 312

[56] References Cited

U.S. PATENT DOCUMENTS

| | | | |
|---|---|---|---|
| 1,359,345 | 11/1920 | Fields | 450/94 |
| 2,250,267 | 7/1941 | Lins | 450/98 X |
| 2,738,789 | 3/1956 | Foxworthy | 450/94 |
| 3,124,137 | 3/1964 | Bradd . | |
| 3,545,446 | 12/1970 | Nobbs | 450/98 |
| 3,623,488 | 11/1971 | Nakayama | 128/95.1 X |
| 4,022,197 | 5/1977 | Castiglia | 128/96.1 X |
| 4,969,216 | 11/1990 | Guelli | 450/98 X |

FOREIGN PATENT DOCUMENTS 2124072 2/1984 United Kingdom .................. 450/94

Primary Examiner—Sam Rimell
Attorney, Agent, or Firm—Fitzpatrick, Cella, Harper & Scinto

[57] ABSTRACT

An umbilical girdle for securing the navel of newborns, and characterized by the fact that it comprises one tubular piece formed from an elastic mesh (1) and provided in its border portions with an elastic edge. The measurements of the girdle in a state of contraction and repose and its degree of elasticity adjust to the measurements of the midsection of the newborn (2), so that when in use it adheres gently but firmly around the abdomen in such a way that it secures a compress (3) and the fastening clip on the stub of the umbilical cord without causing discomfort to the user. The placement and removal of the mesh is performed quickly and simply without having to wrap it around the newborn's body.

1 Claim, 1 Drawing Sheet

FIG. 1
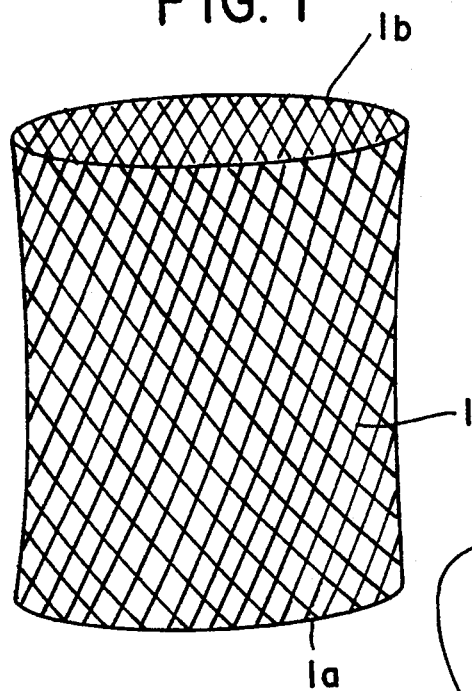
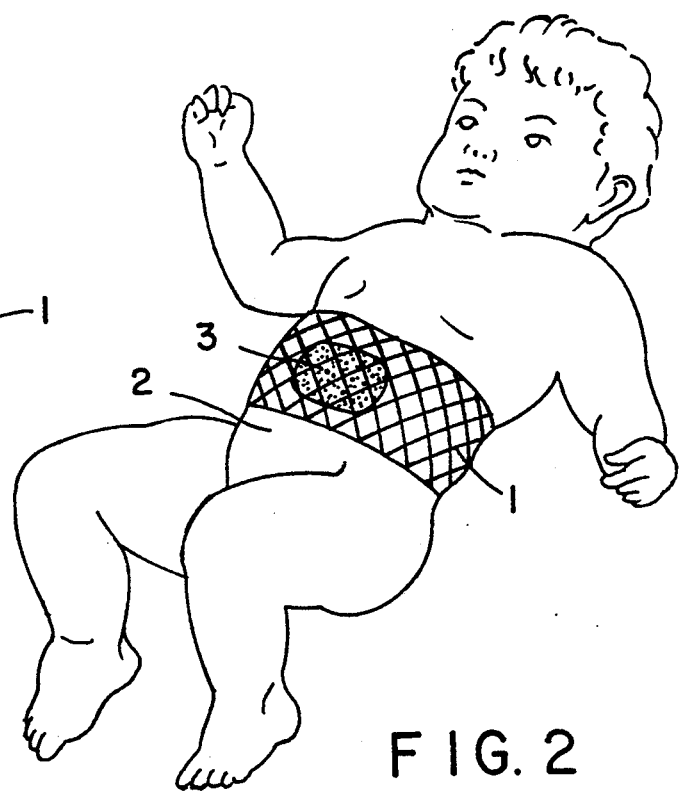
FIG. 2
FIG. 3
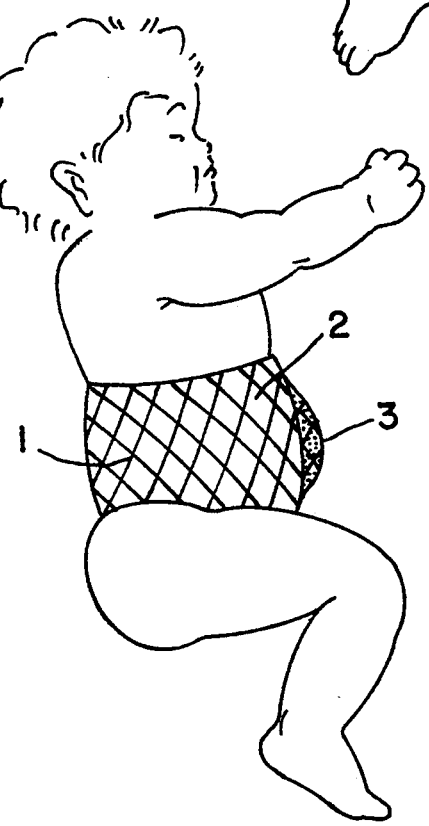

METHOD FOR PROTECTING AN INFANT'S NAVEL

This application is a continuation of application Ser. No. 07/873,657 filed Apr. 23, 1992, and which is a continuation of application Ser. No. 07/573,729, filed Aug. 28, 1990, both now abandoned.

BACKGROUND OF THE INVENTION

The present invention refers to an umbilical girdle for newborn babies, that takes the place of classic bandages that encircle the abdomen of the newborn intended to hold the stump of the umbilical cord and the fastening clip in place.

The bandages that are currently used are inconvenient in that their placement is complicated and they require certain steps in order to secure them in the proper place, such as knotting strips around the midesection of the newborn.

SUMMARY OF THE INVENTION

In order to solve these problems, an umbilical girdle has been designed, an invention of simple construction and very practical use.

The girdle of the present invention is of the type intended to secure the navel of the newborns and is characterised essentially by the fact that it comprises one tubular piece formed from an elastic mesh and is provided in its border portions with an elastic edge.

In a possible working model the tubular piece of fabric will have a compress incorporated in its inner face.

In order to better understand what is described in this petition it is accompanied by a drawing in which, as only one possible example a practical model of the girdle is shown.

BRIEF DESCRIPTION OF THE DRAWINGS

In said drawing FIG. (1) is a view form the perpective of the girdle and FIGS. (2) and (3) are views seen from the perpective of the mesh placed in position.

DETAIL DESCRIPTION OF INVENTION

The girdle described in the drawing consists of a tube formed from an elastic mesh (1), with or without a seam, constructed from rubber and synthetic fibers (polyester), cotton or other material. It can also be made of an elastic cloth of any material such as lycra. Item (1) has protective elastic borders (1a) on its sides which constitute the outer finish of the girdle.

The measurements of the girdle in a state of contraction and repose and its degree of elasticity adjust to the measurements of the midsection of the newborn (2), so that when in use it adheres gently but firmly around the abdomen in such a way that it secures a compress (3) and the fastening clip on the stub of the umbilical cord without causing discomfort to the user.

It has been envisioned that the tubular part (1) be manufactured to be equipped with the compress (3).

The placement and removal of the mesh is perfomed quickly and simply without having to wrap it around the newborn's body.

The object of invention and the materials utilized in its manufacture the shapes and dimensions herein and all of the incidental details that might present themselves will remain independent, provided that these do not affect its essence.

I claim:

1. A method of protecting an infant's navel, comprising the steps of:
   providing an umbilical girdle having a continuous tubular band formed from an elastic mesh with a first border portion and a second border portions, and having an interior portion;
   providing a compress on said interior portion;
   placing the tubular band around a mid-section of the infant; and
   positioning the compress to cover the navel of the infant.

* * * * *

UNITED STATES PATENT AND TRADEMARK OFFICE
CERTIFICATE OF CORRECTION

PATENT NO. : 5,406,964
DATED : April 18, 1995
INVENTOR(S) : Antonio M. Calleja

It is certified that error appears in the above-indentified patent and that said Letters Patent is hereby corrected as shown below:

Title Page:
[76] Inventor:

"Bareelona" should read --Barcelona--.

[56] References Cited

U.S. Patent Documents, "1,359,345" should read --1,359,346--.

COLUMN 1

Line 22, "mide-" should read --mid- --; and

Line 43, "example" should read --example,--.

COLUMN 2

Line 3, "form" should read --from--;

Line 6, "DETAIL" should read --DETAILED--;

Line 27, "invention" should read --this invention--;

Line 28, "manufacture" should read --manufacture,--; and

UNITED STATES PATENT AND TRADEMARK OFFICE
CERTIFICATE OF CORRECTION

PATENT NO. : 5,406,964
DATED : April 18, 1995
INVENTOR(S) : Antonio M. Calleja

It is certified that error appears in the above-indentified patent and that said Letters Patent is hereby corrected as shown below:

Column 2, line 37, "portions," should read --portion,--.

Signed and Sealed this

Fourteenth Day of November, 1995

*Attest:*

BRUCE LEHMAN

*Attesting Officer*     *Commissioner of Patents and Trademarks*